United States Patent [19]

Hoberman

[11] Patent Number: 4,463,098

[45] Date of Patent: Jul. 31, 1984

[54] HEMOGLOBIN MARKER OF ALCOHOLISM

[75] Inventor: Henry D. Hoberman, New Rochelle, N.Y.

[73] Assignee: Albert Einstein College of Medicine of Yeshiva University a Division of Yeshiva University, Bronx, N.Y.

[21] Appl. No.: 538,357

[22] Filed: Oct. 3, 1983

Related U.S. Application Data

[63] Continuation of Ser. No. 196,179, Oct. 14, 1980, abandoned.

[51] Int. Cl.³ .............................................. G01N 33/72
[52] U.S. Cl. ...................................... 436/67; 436/183
[58] Field of Search ................................... 436/67, 183

[56] References Cited

PUBLICATIONS

Stevens et al., "Nonenzymatic Glycosylation of Hemoglobin", *The Journ. of Bio. Chem.*, vol. 252, No. 9 (5-1-0-77).

*Primary Examiner*—Peter Chin

[57] ABSTRACT

An in vitro method for identifying alcoholism and alcohol abuse in humans is disclosed which comprises the isolation and measurement of a unique and stable form of glycosylated hemoglobin.

5 Claims, 3 Drawing Figures

FORMATION OF A RADIOACTIVE ADDUCT BETWEEN HEMOGLOBIN $A_0$ AND $(4-{}^3H)$ DXP.

ANALYSIS OF REACTION MIXTURE CONTAINING RADIOACTIVE DXP AND HEMOGLOBIN $A_0$ ON THE BEGINNING OF THE 2ND DAY OF REACTION. FRACTIONS 1–10 WERE ELUTED WITH 0.04M PHOSPHATE – 0.01 CYANIDE, pH 6.4. HEMOGLOBIN $A_0$, FRACTIONS 11–14, WAS ELUTED WITH 0.3M PHOSPHATE, pH 6.4.

SCATTER PLOT OF VALUES OF THE MINOR HEMOGLOBIN FRACTION IN ALCOHOLIC PATIENTS AND HEALTHY VOLUNTEERS. THE SOLID LINES REPRESENT MEANS AND THE DASHED LINES, STANDARD DEVIATIONS.

HEMOGLOBIN MARKER OF ALCOHOLISM

The U.S. Government has rights in this invention pursuant to Grant No. NIAA & A R01-AA02469.

This is a continuation of Application Ser. No. 196,179 filed Oct. 14, 1980.

FIELD OF THE INVENTION

This invention relates to a method for measuring alcohol intake in humans. This invention further relates to a method for providing a dose-time record of alcohol consumption.

BACKGROUND AND DISCUSSION OF PRIOR ART

To the present time, efforts to identify markers of alcoholism have relied chiefly on evaluating changes in liver biochemistry reflected in the blood by changes in the concentrations of certain amino acids. See Shaw, et al, 1976, Plasma a-amino-n-butyric acid to leucine ratio: An empirical biochemical marker of alcoholism, *Science*, 194: 1057.

Accumulating evidence indicates, however, that probes that depend on the development of abnormalities of liver function lack the specificity required of a test that, in principle, should do no more than reflect a dose-time record of alcohol consumption. See Morgan, M. Y., et al, 1977, Ratio of plasma a-amino-n-butyric acid to leucine as an empirical marker of alcoholism: Diagnostic value, *Science*, 197: 1183; Eriksson, S., et al, 1979, Plasma a-amino-n-butyric acid/leucine ratio in alcoholism, *N. Eng. J. Med.* 300L 93; Kristensson, H., et al, 1977, Serum glutamyl-transferase in alcoholism, *Lancet*, 1: 609; and Whitehead, T. P., et al, 1978, Biochemical and hematological markers of alcohol intake, *Lancet*, 1: 978.

Now, there is provided by the present invention a method for providing an accurate in vitro test which will identify alcoholism in humans.

It is a further object of this invention to provide a method for obtaining an objective and quantitative measure of alcohol consumption over varying periods of time.

It is an additional object of this invention to provide a method for obtaining an objective and qualitative measure of alcohol consumption which does not rely on detecting hepatoxic effects of ethanol made evident by blood tests of liver function.

The aforesaid objects as well as other objects and advantages, will be made more apparent in reading the following description and the enjoined claims.

DESCRIPTION OF THE PREFERRED EMBODIMENTS

Figure 1:
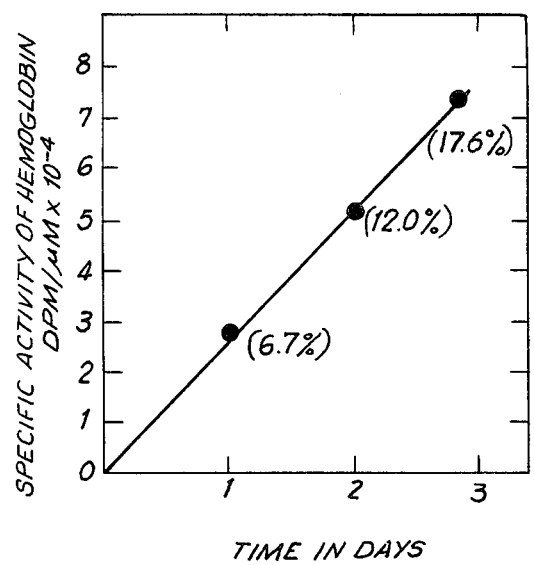
FIG. 1 shows the formation of a radioactive adduct between hemoglobin $A_o$ and (4-$^3$H) DXP
Figure 3:
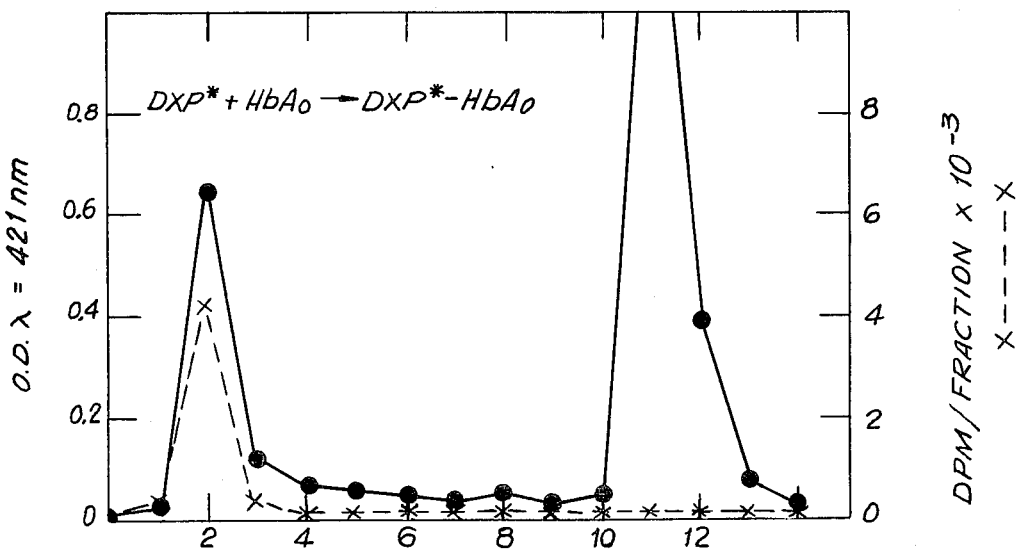
FIG. 3 shows analysis of a reaction mixture containing radioactive DXP and hemiglobin $A_o$ on the beginning of the 2nd day of reaction.

Broadly speaking, the method of the present invention is for detecting and measuring alcohol intake in humans, comprising:

a. obtaining a blood sample from a patient;

b. isolating a fraction of said blood sample which contains glycosylated hemoglobin;

c. measuring the degree or level of said glycosylated hemoglobin in the blood sample; and d. comparing the measurement of step "c" with known degrees of said glycosylated hemoglobin in blood samples from others who consume from zero to significant amounts of alcohol daily, whereby the measured degree of the glycosylated hemoglobin in the patient's blood sample is indicative of the level of alcohol consumption by said patient.

The glycosylated hemoglobin herein is a unique and stable form resulting from the reaction between hemoglobin Ao (HbAo) and the compound 5-deoxy-D-xylulose-1-phosphate (DXP) produced by red blood cells (See H. D. Hoberman, 1979, Synthesis of LiDHAP (Sigma), 2 ml of 0.5M TEA-0.001M EDTA, pH 7.6, and 20 mg of aldolase (Sigma 100 units/mg) dissolved in 2.5 ml of 0.1M TEA-0.0002M EDTA, pH 7.6, were mixed in a glass stoppered centrifuge tube that was then kept at 37° for 3 hours. After cooling the reaction mixture in ice, aldolase was precipitated with cold perchloric acid, the solution neutralized with KOH to remove perchlorate, and then lyophilized. The residue was extracted with small portions of cold water, which were combined. From this solution radioactive DXP was isolated by chromatography on Dowex-1-formate. Using this procedure (Hoberman, H. D., 1965, *Ann. N.Y. Acad. Sci.* 119: 1070–1081), which employs a 0–6N gradient of formic acid to elute anions less acidic than simple phosphate esters, DXP was eluted by passing 6N formic acid through the column after gradient elution had ended. The DXP fraction was pooled and lyophilized. The residue was dissolved in 10 ml of water and the solution brought to pH 7.01 by adding solid bis-Tris (Sigma). The concentration of DXP, determined by enzymatic analysis (Hoberman, H. D., 1979, *Biochem. Biophys. Res. Comm.* Paper 1), was 11.6 mM and the specific activity, $4.21 \times 10^5$ dpm/$\mu$mole, a radioactive yield of 47%.

Hemoglobin Ao: This was prepared from a hemolysate of freshly drawn heparinized venous blood of a health donor by chromatography on Biorex 70 as described by McDonald, et al, 1978, *J. Biol. Chem.* 235: 2327–2332. Hemoglobin concentration was measured by the method of Drabkin, 1949, *Am. J. Med. Sci.* 217: 710–711.

Reaction between hemoglobin Ao and (4-$^3$H) DXP: 2.0 ml of (4-$^3$H) DXP (23.2 $\mu$moles) were added to 5.0 ml of 2.35 mM hemoglobin Ao (11.8 $\mu$moles) dissolved in 0.14M NaCl-0.001M 5-deoxy-D-xylulose-1-phosphate by human erythrocytes, *Bio-chem, Biophys. Res. Comm.*, 90: 757–763) in the presense of added acetaldehyde (AcH), which is the primary oxidation product of ethanol and endogenous dihydroxyacetone phosphate (DHAP).

By the term "degree" or "level" as used hereinbefore and hereinafter throughout the specifications and claims, it is meant the percent of hemoglobin Al comprising specific glycosylated hemoglobin to the total hemoglobin present.

More specific aspects of the invention disclosed herein are detailed in the experiments below.

EXPERIMENT I

The materials and methods used in this experiment are detailed below:

(1-$^3$H) acetaldehyde: This was prepared by oxidation of (2-$^3$H) analine (Hoberman, H. D., et al, 1960, *J. Biol.*

Chem. 235: 514–518) with ninhydrin, as described by Arnstein and Crawhill for the synthesis of tritiated formaldehyde from tritiated glycine (Arnstein, H. R. V., et al, 1957, Biochem. J. 67: 180–187) but with the exception that, before distilling over acetaldehyde, 50 ml of water were added to the reaction mixture. From 5.0 mmoles of ($2\text{-}^3$H) alanine, having a specific activity of $4.1 \times 10^5$ dpm/$\mu$mole were obtained 60 ml of an aqueous solution of 26.0 mM ($1\text{-}^3$H) acetaldehyde having a specific activity of $4.00 \times 10^5$ dpm/$\mu$mole, a radioactive yield of 30%. Acetaldehyde was assayed with yeast alcohol dehydrogenase (Racker, E., 1957, *Methods in Enzymology*, Vol. III, pp. 295–296, Academic Press, N.Y.).

($4\text{-}^3$H) DXP: 10 ml of ($1\text{-}^3$H) acetaldehyde, 50 mg of bis-Tris, pH 7.00. The concentration of DXP in this solution was thus 3.3 mM and of hemoglobin Ao, 1.69 mM. The solution was sterilized by passage through a 0.45 micron membrane filter and collected in a sterile container which was then placed in a 37° water bath. Each day for 3 consecutive days aliquots were withdrawn, taking sterile precautions, for measurement of the radioactivity of any DXP-hemoglobin adduct that may have formed. Hemoglobin concentration was also determined.

Precipitation of hemoglobin: To 0.1 ml of sample were added 0.1–0.2 ml of 30% hydrogen peroxide. The frothy mixture was stirred with a glass rod until the hemoglobin was completely bleached. The decolorized hemoglobin was then dissolved in 2.0 ml of water, adding 0.05–0.1 ml of 1M NaOH when needed to form a clear solution, and then precipitated by addition of 2.0 ml of 10% trichloroacetic acid. The flocculent precipitate was sedimented by centrifugation, the resulting pellet dissolved as before, and the protein again precipitated with trichloracetic acid. By carrying out this procedure for a third time, virtually all non-protein radioactivity was removed. To assay the decolorized hemoglobin for radioactivity, a 1 ml aliquot was withdrawn from 2.05–2.10 ml of hemoglobin solution and pipetted into 10 ml of a compatible scintillation mixture (Hydromix). Because of short-lived scintillations unrelated to the radioactivity of the sample, counting was carried out overnight. To correct for quenching the samples were recounted after adding an internal standard. Agreement between duplicate analyses was within 2%.

Chromatographic separation of hemoglobins: Separation of hemoglobins in the reaction mixture was carried out by the method of Trivelli, Ranney, and Lai, 1971, *N. Engl. J. Med.* 284: 353–357, as modified by Gabbay, et al, 1977, *J. Clin. Endocrinol. Metab.* 44: 859–846.

This experiment showed that a radioactive product, stable to precipitation by trichloroacetic acid, was formed by reaction of labeled DXP with hemoglobin Ao. A plot of the specific activity of hemoglobin as a function of reaction time gave the straight line shown in FIG. 1. The values in parentheses express, in percent, the proportion of total hemoglobin that had formed on adduct with DXP. They were calculated by dividing the specific activity of hemoglobin at each time point by the specific activity of labeled DXP and multiplying the result by 100. In making this calculation it was assumed that DXP combined with hemoglobin in a 1:1 molar ratio.

On the beginning of the second day of the experiment an aliquot of the reaction mixture was withdrawn and dialyzed for 24 hours at 4° against 500 volumes of 0.04M Na phosphate, 0.01M KCN, pH 6.6. Separation of hemoglobins from this solution was then carried out as indicated above. Coincident peaks of radioactivity and optical density appeared in the chromatogram soon after elution with dilute phosphate-cyanide was begun. In this respect DXP-hemoglobin was indistinguishable from phosphate-containing hemoglobins normally found in hemolysates of human erythrocytes (Trivelli, L. A., et al, 1971, *N. Engl. J. Med.* 284: 353–357; and Gabbay, K. H., et al, 1977, *J. Clin. Endocrinol. Metab.* 44: 859–864).

From values of the absorbance at 421 nm of the DXP-hemoglobin and hemoglobin Ao fractions, it was determined that DXP-hemoglobin comprised 6.4% of the total, a value in good agreement with that calculated from the specific activity of hemoglobin isolated from the reaction mixture at the end of the first day of incubation. However, although this result suggested that the radioactive fraction consisted only of DXP-hemoglobin, the specific activity of the fraction was found to be $3.0 \times 10^5$ dpm/$\mu$mole, corresponding to 71% rather than 100% purity.

($4\text{-}^3$H) DXP was found to react with hemoglobin Ao to form a radioactive adduct stable to repeated precipitation by trichloroacetic acid and to 24 hour dialysis against dilute phosphate-cyanide buffer. Formation of a DXP-hemoglobin adduct to the extent of 17.6% in 3 days at 37° indicates that the affinity of DXP for hemoglobin is greater than has so far been observed in experiments with other phosphate esters. An interesting example for comparison is fructose-1-phosphate, whose steric configuration from C1 to C4 is the same as that of the corresponding carbon atoms of DXP. Under conditions not remarkably different from those presently employed, fructose-1-phosphate combined with hemoglobin Ao to the extent of 9.8% (Stevens, V. J., et al, 1977, *J. Biol. Chem.* 252: 2998–3002). It is tempting to speculate that the greater affinity of DXP for hemoglobin relates to the fact that DXP has an open-chain configuration whereas fructose-1-phosphate exists predominantly as the furanoside. Thus, in contrast with DXP, a ring must open before fructose-1-phosphate can react to form a Schiff base, creating the bond which, it is widely assumed, is responsible for the glycosylation of hemoglobin by a variety of sugar phosphates.

Having observed that DXP is formed in human red blood cells exposed to acetaldehyde and that it is bound by hemoglobin, formation in vivo of a DXP-hemoglobin adduct would serve to integrate the concentration of acetaldehyde in the blood and thus reflect a dose-time record of alcohol consumption. In this connection, it is of interest that, when the blood of a nondiabetic individual who had been drinking heavily for a month was analyzed for hemoglobins by the Trivelli-Gabbay procedure, 20% of the total hemoglobin was eluted in the phosphate-containing hemoglobin fraction.

EXPERIMENT II

If DXP-hemoglobin were to be formed in vivo, it would be found among the minor hemoglobins, Ala1, Ala2, Alb, and Alc. This is because its anionic charge, mainly due to the phosphoric acid residue attached to deoxylulose, is, like the hemoglobin Al fraction, greater than the charge on hemoglobin Ao, the major component of hemoglobin A. When analyzed by methods of ion-exchange chromatography currently in use for the rapid estimation of hemoglobin Alc (See, Gabbay K. H., et al, 1977, Glycosylated hemoglobins and long-term glucose control in diabetes mellitus. *J. Clin. Endocrinol Metal.* 44: 859–864; and Abraham E. C., et al, 1978, Determination of glycosylated hemoglobins (HbAl) with a new microcolumn procedure. *Diabetes.* 27: 931–937) DXP-hemoglobin that has been added to a human hemolysate is recovered with the minor hemoglobins. This suggested that a search for DXP-hemoglobin in in vivo might best begin by comparing the sizes of minor hemoglobin fractions in alcoholic and nonalcoholic men and women.

The 48 patients who took part in this study were men and women admitted to a Comprehensive Alcohol Treatment Center who gave informed written consent to taking part in the investigation. Hospitalization was based on a patient's request for help with his or her drinking problem. Omitted from consideration individuals later found to be diabetes mellitus or serum glucose concentrations above 115 mg/dl (6.4 mM). After these exclusions there remained 6 women and 37 men in the alcoholic group. Their ages ranged between 19 and 65 years and averaged 35 years.

The 41 healthy volunteers were 18 women and 23 men whose ages were 16 to 66 years, averaging 32 years. Less than 10 percent of this group, which included students, fellows, faculty, and laboratory helpers and technicians, denied consumption of alcohol beverages of any kind.

Patients' blood samples were collected on the day of admission for minor and total hemoglobin analyses, complete blood count, and SMA-6 and SMA-12 analyses. For the hemoglobin determinations blood was drawn into heparinized tubes and analyzed for total hemoglobin by the Drabkin procedure (See, Drabkin D. L., 1946, Spectrophotometric studies. XIV. The crystallographic and optical properties of the hemoglobin in man in comparison with those of other species. *J. Biol. Chem.* 164: 703–723) and for the minor hemoglobin fraction by the microcolumn (Isolab, Inc., Akron, Ohio) method employed by Abraham, et al (See Abraham. E. C., et al, 1978, Determination of glycosylated hemoglobins (HbAl) with a new microcolumn procedure. *Diabetes.* 27: 931–937). Hemolysates, prepared according to the direction of Geraci, et al (See Geraci G., et al, 1969, Preparation and properties of $\alpha$-and-$\beta$-chains from human hemoglobin. *J. Biol. Chem.* 244: 4664–4667), were stored in a liquid $N_2$ refrigerator until analyzed for hemoglobin Alc by the method of Flückiger and Winterhalter (See, Flückiger R., et al, 1976, In vitro synthesis of hemoglobin Alc. *FEBS Letters.* 71: 356–360). The optical density at 443 nm was multiplied by 6.9 to obtain the amount of hemoglobin Alc in mg/ml (Dr. R. Flückiger, personal communication).

Plasma ethanol concentrations were measured by an enzymatic, automated, fluorometric method based on the procedure developed by Antonis, et al (See, Antonis A., et al, 1966, A semi-automatic fluorometric method for the enzymatic determination of pyruvate, lactate, acetroacetate, and B-hydro-xybutyrate levels in plasma. *J. Lab. Clin. Med.* 68: 340–356).

Control blood samples were analyzed for total hemoglobin as well as for the minor hemoglobin fraction.

Figure 2:
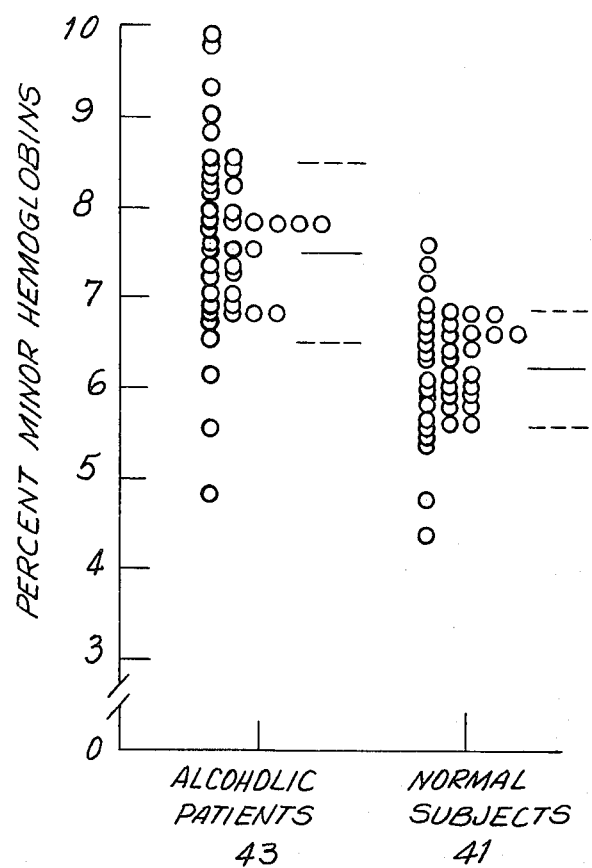
FIG. 2 shows values of minor hemoglobin fraction for alcoholic patients and healthy subjects

Values of the minor hemoglobin fraction in the 43 patients and 41 healthy subjects are shown graphically in FIG. 2. In the alcoholic patients the proportion of minor hemoglobins was significantly above normal, the minor fraction accounting for $6.2\pm0.64$ (S.D.) percent of the total hemoglobin in normal individuals and $7.5\pm0.98$ (S.D.) percent in alcoholic patients ($P<0.0001$). Normal mean values reported here are not significantly different from those obtained by Trivelli, et al (See, Trivelli L. A., et al, 1971, The relation of components in patients with diabetes mellitus. *N. Engl. J. Med.* 284: 353–357), using a modification of the method of Schnek and Schroeder (See Schnek A. G., et al, 1961, The relation between the minor components of whole normal human adult hemoglobin as isolated by chromatography and starch block electrophoresis. *J. Amer. Chem. Soc.* 83: 1471–1478).

Eleven alcoholic patients had values of the hemoglobin Al fraction that were greater than 3 S.D. above the normal mean, i.e. values equal to or greater than 8.2 percent. Samples of the plasma of these patients contained no detectable amount of ethanol (less than 1 $\mu$mole/ml) indicating that drinking of alcoholic beverages had ceased several days before admission. Values of the minor hemoglobin fraction, total hemoglobin, serum glucose concentrations, serum liver enzyme activities, and age and sex in this group of 11 patients are shown in Table 1.

TABLE 1

Values of serum enzyme activities, blood sugar concentration, minor and total hemoglobins, age and sex of 11 patients whose values of the minor hemoglobin fraction were equal to or exceeded 8.2 percent.

| Patient | Sex | Age | LDH | SGOT Units/ml | SGPT | Serum glucose mg/dl | Minor Hb fraction percent | Total Hb g/dl | |
|---|---|---|---|---|---|---|---|---|---|
| P. S. | F | 29 | 214 | 40 | 45 | 75 | 9.3 | 13.8 | |
| S. A. | F | 32 | 900 | 365 | 91 | 65 | 9.0 | 12.1 | |
| E. G. | M | 37 | 249 | 66 | 103 | 90 | 8.3 | 17.5 | |
| W. B. | M | 32 | 165 | 43 | 46 | 109 | 8.4 | 13.9 | |
| M. H. | M | 35 | 293 | 104 | 72 | 80 | 8.5 | 14.9 | |
| I. A. | F | 44 | 537 | 44 | 23 | 100 | 8.4 | 14.7 | |
| J. S. | M | 39 | 398 | 150 | 120 | 75 | 8.7 | 11.3 | |
| S. B. | M | 65 | 267 | 10 | 21 | 65 | 8.2 | 15.8 | |
| G. P. | F | 37 | 405 | 120 | 135 | 99 | 8.5 | 13.8 | |
| R. B. | M | 38 | 383 | 178 | 75 | 62 | 9.7 | 15.6 | |
| C. C.* | F | 42 | 268 | 206 | 180 | 79 | 9.3 | 14.2 | |
| Normal range | | | 100–225 | 8–40 | 7–40 | 60–115 | 4.3–7.6 | M 16 F 14 | $\pm2$ |

*Patient C. C.'s erythrocytes had a mean corpuscular volume of 111 $\mu^3$. Values of the MCV in the other 10 patients ranged between 85.6 and 97.3 $\mu^3$ and averaged 93.9 $\mu^3$.

Directing attention to serum enzyme activities, although in most cases, one or more values were abnormal. 3 patients (P. S., W. B., and S. B.) did not have significant elevations of these enzymes, indicating absence of concordance between size of the hemoglobin Al fraction and liver function. This observation is in agreement with findings reported by Dolhofer, et al. (See Dolhofer R., et al, 1977, Clinical and biochemical studies on the significance and formation of hemoglobins Alc and Ala+b in diabetes mellitus. Klin Wochenschr. 55: 945-954), showing that values of the minor hemoglobin fraction were within normal limits in patients with liver disease.

The normal serum glucose concentrations in Table 1, indicates that the greater size of the minor hemoglobin fraction in alcoholic than in nonalcoholic individuals was not likely to have been due to increased production of hemoglobin alc. This was borne out by analysis of the hemolysates for hemoglobin Alc. Using the method of Flückiger and Winterhalter (See, Flückiger R., et al, 1976, In vitro synthesis of hemoglobin alc. FEBS Letters. 71: 356-360), it was found that hemoglobin Alc accounted for between 1.9 and 3.6 percent of the total hemoglobin, averaging 2.7±0.49 (S.D.) percent. Using the Trivelli procedure, Dolhofer, et al (See Dolhofer R., et al, 1977, Clinical and biochemical studies on the significance and formation of hemoglobin Alc and Ala+b in diabetes mellitus. Klin Wochenschr. 55: 945-954) found that hemoglobin Alc normally comprised from 3.1 to 5.9 percent of the total hemoglobin, averaging 4.5 percent. The results thus indicates that in normoglycemic alcoholic persons, hemoglobin Alc comprises no more, and perhaps less, of the total hemoglobin than normal. The same can be said of the other components of the hemoglobin Al fraction, whose concentrations are also influenced by the blood sugar concentration. Hence the results suggest that in alcoholism, the proportion of minor hemoglobins is made larger by the presence of a hemoglobin adduct whose formation is uniquely dependent on excessive consumption of alcohol.

Of the 6 women in the group of alcoholic patients, 5 were among the 11 patients having the highest values of the hemoglobin Al fraction. Control men and women did not differ from each other in respect to the size of the minor hemoglobin fraction and when the 6 female patients were matched for age with control women, the difference in values was even greater than between the mixed populations. These observations raise questions about the influence of the sex of an alcoholic individual on alcohol metabolism and drinking habits.

Spontaneous formation of a hemoglobin adduct is a function not only of the instantaneous concentration of the agent that becomes attached to hemoglobin but also of the length of time during which its concentration remains high enough to sustain the reaction. Thus, to establish a quantitative relation between the increase in size of the minor hemoglobin pool and alcohol consumption, one must know the quantity of alcohol consumed at a given time and as a function of time. Information about these matters that is as accurate as is the information about the size of the minor hemoglobin fraction cannot be obtained from alcoholic patients. Despite this the minor hemoglobin fraction is a reflection of the dose-time record of alcohol consumption by an individual and thus can be more accurately related to steps in the pathogenesis of alcoholism and its clinical manifestations than can a historical account of drinking habits.

It should not be so difficult to obtain measurements on alcoholic patients showing the decline of the minor hemoglobin fraction after abstention from drinking. In theory, the time required for return of the fraction to normal size is equal to the lifespan of the erythrocyte. The time needed to observe an analytically significant fall is thus measured in weeks. Although there are no measurements showing this change, in the longest period that has thus far elapsed between analyses on the same alcoholic individual, no decline from an initial value of 10.5 percent was found to occur over the 3 week interval, presumptive evidence that drinking had continued.

The results herein indicate the use of measurements of the minor hemoglobin fraction for screening for excessive alcohol consumption. The analyses should further be of help in the differential diagnosis of liver disease and other disorders associated with alcoholism. They may reveal unsuspected or unrecognized compulsive drinking, providing grounds for medical intervention, and thereby serve as a preventive measure. They may be used to follow the progress of treatment.

EXPERIMENT III

When 2 molar equivalents of radioactive DXP were added to a solution containing 1 molar equivalent of hemoglobin Ao (HbAo), i.e. normal hemoglobin from which minor hemoglobins have been removed, a radioactive hemoglobin derivative was formed (Hoberman, 1979b). The product was stable to dialysis for 24 hours against 0.04M phosphate-0.01M cyanide, pH 6.4, and to repeated precipitation by trichloroacetic acid. The specific activity of hemoglobin precipitated from the reaction mixture increased linearly with time and by the end of the third day at 37° had reached a value which indicated, when compared with the specific activity of radioactive DXP, that 17.6% of hemoglobin Ao had formed a derivative with DXP.

DXP-hemoglobin was readily separable from unreacted hemoglobin Ao by chromatography on the polyacrylic acid resin, Biorex 70, following the directions of Trivelli (See, Trivelli, L. A., et al, 1971, Hemoglobin components in patients with diabetes mellitus, N. Eng. J. Med. 284: 353), as modified by Gabbay (See Gabbay, K. H., et al, 1977, Glycolsylated hemoglobins and long-term glucose control in diabetes mellitus. J. Clin. Endocrinol. Metab. 44: 859). FIG. 1 shows the results of an analysis of 0.1 ml of reaction mixture at the beginning of the second day of reaction. Attention is called to the overlap of peaks of absorbancy and radioactivity. From the values of the absorbancy and radioactivity of this peak, it was estimated that 71% of the hemoglobin in this fraction was in the form of a DXP-hemoglobin adduct.

The basic method underlying this experiment and the invention disclosed herein may be broken down into steps comprising:
  a. an anticoagulated blood specimen is obtained from a patient;
  b. red blood cells from said specimen are taken and a hemolysate is prepared by osmatic shock;
  c. the hemolysate of step b is loaded onto a Biorex 70 chromatography column;
  d. the hemoglobin adducts are separated by the techniques of Trivelli, et al (1971), as modified by Gabbay, et al (1977); and
  e. column fractions are collected and monitored at 421 nm.

In the specification above there has been set forth a preferred embodiment of the intention and, although specific terms employed, they are used in a generic and descriptive sense only and not for purposes of limitation.

Inasmuch as many changes could be made in the above procedures, and many apparently different embodiments of the invention could be made without departing from the scope thereof, it is intended that all matters contained in the above description shall be interpreted as illustrative and not in a limiting sense.

What is claimed is:

1. A method for detecting and measuring chronic alcohol consumption constituting alcohol abuse in a human patient comprising:
    a. obtaining a human blood sample from said patient;
    b. isolating a fraction of said blood sample which contains glycosylated hemoglobins;
    c. measuring the amount of said glycosylated hemoglobins as a percentage of the total amount of hemoglobin in said sample;
    d. providing a measurement of the amount of glycosylated hemoglobins in a blood sample of a known alcohol abuser, the measured amount of the glycosylated hemoglobins of said abuser being more than about 6% of the total hemoglobin in said blood sample of the abuser; and
    e. comparing the measurements of steps (c) and (d) whereby a comparison of said measurements determines the alcohol abuse of said patient.

2. The method of claim 1, wherein the patient's blood sample comprises anticoagulated blood.

3. Method of claim 1, wherein step (b) thereof further comprises:
    (i) exposing the red blood cells of step (i) hereof to osmotic shock, whereby a hemolysate is prepared; and
    (ii) separating the hemoglobin adducts of step (i) hereof by chromatography.

4. The method of claim 1, wherein the measurements of step (c) are performed by a colorimetric assay.

5. The method of claim 4, wherein the assay is performed at 421 nm.

* * * * *